(12) United States Patent  (10) Patent No.: US 8,747,429 B2
Peyman  (45) Date of Patent: Jun. 10, 2014

(54) SCLERAL BUCKLING PROCEDURE AND DEVICE

(76) Inventor: Gholam A. Peyman, Sun City, AZ (US)

( * ) Notice: Subject to any disclaimer, the term of this patent is extended or adjusted under 35 U.S.C. 154(b) by 116 days.

(21) Appl. No.: 13/213,432

(22) Filed: Aug. 19, 2011

(65) Prior Publication Data

US 2013/0046325 A1  Feb. 21, 2013

(51) Int. Cl.
A61M 29/00 (2006.01)
A61B 19/00 (2006.01)

(52) U.S. Cl.
USPC .......................................... 606/192; 128/898

(58) Field of Classification Search
USPC ................. 606/191, 192, 194, 195, 198, 202; 604/96.01
See application file for complete search history.

(56) References Cited

U.S. PATENT DOCUMENTS

| 4,299,227 | A | * | 11/1981 | Lincoff | 606/192 |
| 4,836,204 | A | * | 6/1989 | Landymore et al. | 606/215 |
| 5,169,386 | A | * | 12/1992 | Becker et al. | 606/192 |
| 5,286,261 | A | * | 2/1994 | Roizenblatt | 606/192 |
| 2004/0039253 | A1 | * | 2/2004 | Peyman et al. | 600/201 |
| 2006/0167422 | A1 | * | 7/2006 | Shahinpoor et al. | 604/294 |
| 2008/0027304 | A1 | * | 1/2008 | Pardo et al. | 600/399 |
| 2009/0299374 | A1 | * | 12/2009 | Tilson et al. | 606/94 |

* cited by examiner

Primary Examiner — Tuan V Nguyen
(74) Attorney, Agent, or Firm — The Law Office of Patrick F. O'Reilly III, LLC

(57) ABSTRACT

A resilient catheter includes a segmental balloon sized and configured so as to be capable of being directed under the conjunctiva toward a retinal tear, the segmental balloon further configured to produce a buckle inside the eye once inflated, and capable of being separated from a remaining part of the catheter while the segmental balloon is left in place for a period of time so as to heal the retinal tear.

19 Claims, 2 Drawing Sheets

SCLERAL BUCKLING PROCEDURE AND DEVICE

BACKGROUND OF THE INVENTION

1. Field of Invention

The present invention is related to a device and method for scleral buckling surgery, which is a surgical procedure to close retinal tears causing retinal detachment.

2. Description of Related Art

Generally, during conventional scleral buckling surgery, the conjuctival tissue is completely dissected away to expose the whitish part of the eye (the sclera). Then a strip of flexible silicone or a silicone sponge is sutured to the outer part of the sclera or under a flap created from the sclera. This buckle indents the outer part of the eye wall to come in close contact with the detached retina inside the eye. The retinal tear that now lies on the indented eye wall (buckle) is coagulated with laser to create scar tissue holding the retina in place and sealing the retinal tear. The buckling element is left in place permanently sutured to the sclera. The dissected conjunctiva is then re-sutured back on its place to cover the soft silicone strip.

The disadvantages of this procedure are that it is time consuming for the doctor and the patient that requires general anesthesia. Although local anesthesia can be performed, because of potential pain sensation duration the surgery which varies between 45-60 minutes, general anesthesia is preferred.

Moreover, the dissected conjunctiva is red, swollen and generally takes a long time to return to normal. Excessive scarring makes secondary surgery difficult and hemorrhagic. The extent of the wound is also prone to access by bacteria which can gain access to the buckle and infect it with serious complications.

Furthermore a permanent buckle which can be 90-360 degrees (e.g., ring) around the eye can cause changes in the refractive shape of the cornea and elongate the eye causing significant myopic (near sited) shift and astigmatism of the refractive power of the eye.

SUMMARY OF THE INVENTION

The present invention is directed to a resilient catheter including a segmental balloon sized and configured so as to be capable of being directed under the conjunctiva toward a retinal tear, said segmental balloon further configured to produce a buckle inside the eye once inflated, and capable of being separated from a remaining part of the catheter while the segmental balloon is left in place for a period of time so as to heal the retinal tear.

DETAILED DESCRIPTION OF THE INVENTION

It is the intention of this invention to develop a temporary buckle that can cover 90-360 of the eye, implanted in a minimally invasive manner and which can be easily removed in the office after a period of a month and beyond if needed; after the retinal rear has scarred. The implant is preferably not exposed to outside space of the conjunctiva to reduce any chance of infection. The procedure can be performed in all patients under local anesthesia within 5-10 minutes potentially in the doctor's office.

Figure 1A:
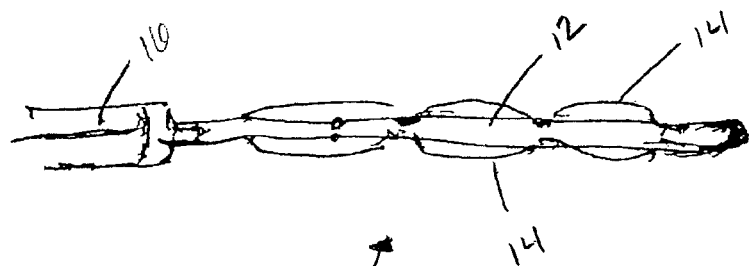
FIG. 1A illustrates a segmented balloon catheter.
Figure 1B:
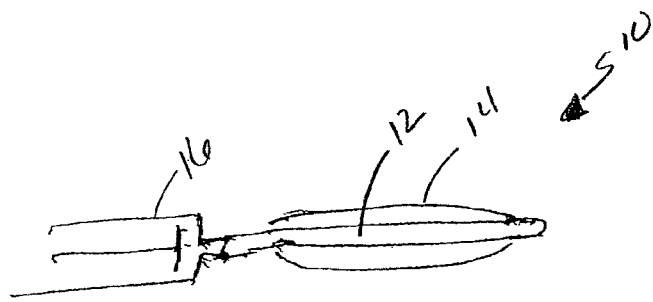
FIG. 1B illustrates a segmented balloon catheter with a single segment.

As shown in FIG. 1A, one embodiment of a buckle 10 is designed in which segmental uniform balloons 14 are connected to a resilient tube 12, similarly to an angioplasty catheter. The balloons 14 may be made of any flexible resilient material such as strong latex, soft silicone or any other flexible biocompatible polymer. Additionally, as shown in FIG. 1B, in another embodiment, one segmental uniform balloon 14 may be connected to the resilient tube 12. A syringe 16 may be connected to the tube 14, if desired.

The balloons 14 can be inflated depending on the desired force and extended so that it is inflated to an oval structure. The tube and balloon can be inflated to a diameter of 3-7 mm and can have a length of 5-40 mm, or any other suitable diameter. This preferred diameter permits the tube and balloon to exert pressure locally or 360 degrees around the eye as needed. A section of the tube can be disconnected, clamped with a miroclamp or tied with a suture and cut at specific distances of 10-45 mm usually about 15 mm for segmental, and more for the encircling one and not lose the pressure in the balloon.

Surgical Technique

Figure 2:
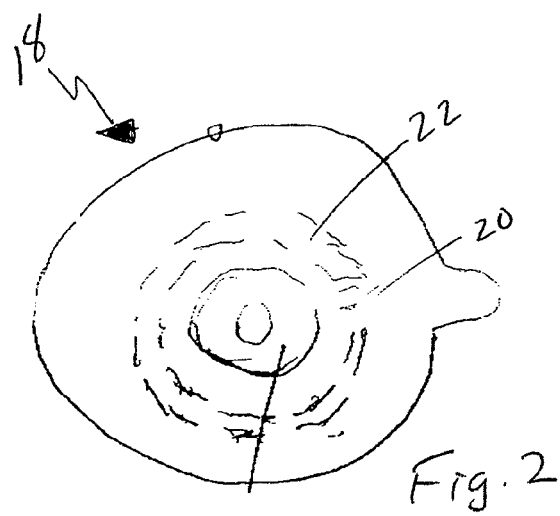
FIG. 2 shows the location of the balloon after surgery under the recti muscles and the conjunctiva.
Figure 3A:
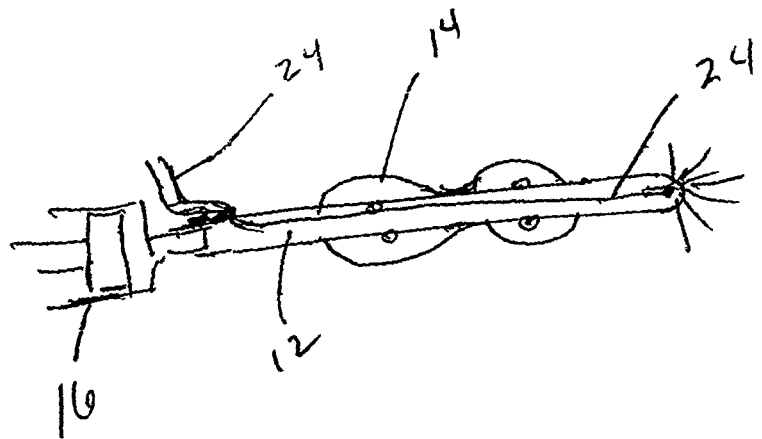
FIG. 3A illustrates a fiber optic connected to the catheter.
Figure 3B:
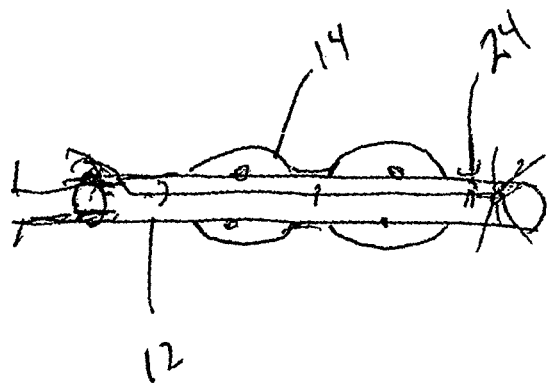
FIG. 3B illustrates a second embodiment of the fiber optic connected to the catheter.

As shown in FIG. 2, after injection of local anesthesia which is done in the retobulbar space behind the eye 18 or under the conjuctive, usually the conjuctival tissue is loosened and somewhat elevated from the sclera. The position of the retinal hole is determined on the eye by indirect ophthalmoscopy and marked with a dye or diathermy. A small <3 mm incision 20 is made at the desired clock hour e.g. 3 and 9 o'clock position to access subconjuctival space. Then the catheter is introduced in the subconjuctival space 22 toward the direction of the retinal tear by gradually ballooning intermittently the front section of the catheter to expand the conjunctiva as the catheter is pushed gradually forward toward the re retinal tear up to 360 degree of the eye. As shown in FIGS. 3A and 3B, the catheter can be guided under the conjunctiva, as seen from outside or inside the eye using a fiber optic illumination 24, indicating the position of the catheter's tip during the surgery or prior to completely inflating the balloon. The fiber optic 24 can be disposed in side of the catheter (FIG. 3A) or outside the catheter (FIG. 3B). the fiber optic 24 can be attached in the catheter in any suitable manner.

Then the desired balloon portion of the balloon is inflated to indent the eye wall creating a buckle inside the eye by observation through an ophthalmoscope. The balloon can be filled with a solution containing medication or therapeutic solutions, such as antibiotics or inti-inflammatory agents etc., or any other suitable fluid or fluids. Once the buckle is in place, some intraocular fluid is removed from the anterior chamber of the eye with a 30 gauge needle to reduce the pressure rise in the eye. At this time the desired section of the tube is discounted and left in place under the conjunctiva. It is of importance to note that the balloon can be filled with air, gas or material with low viscosity like hyaloronic acid, low viscosity polymers such as silicone oil etc. At the end of the surgery the conjunctiva is sutured with nylon or an absorbable suture presently available.

What is claimed is:

1. A resilient catheter comprising:
   a resilient tube;

a plurality of segmental balloons connected in series to said resilient tube, and being sized and configured so as to be capable of being directed under the conjunctiva and above the sclera toward a retinal tear, each of said plurality of segmental balloons having balloon portions disposed on opposite sides of said resilient tube; said resilient tube extending through a central portion of each of said plurality of segmental balloons; said plurality of segmental balloons further configured to produce at least one buckle inside the eye once inflated by said resilient tube, and capable of being separated from a remaining part of said catheter while said plurality of segmental balloons are left in place for a period of time so as to heal the retinal tear;

a fiber optic attached to an outside or inside of said resilient tube so as to enable viewing of the path of said resilient tube under the conjunctiva and the location of said resilient tube inside the eye, said fiber optic being configured and arranged to be removed from said resilient tube after surgery so as to leave said plurality of segmental balloons in place; and a clamp or a suture for closing said resilient tube so as to prevent a pressure loss in said plurality of segmental balloons.

2. The resilient catheter of claim 1, wherein said plurality of segmental balloons are flexible inflatable polymer.

3. The resilient catheter of claim 1, wherein said plurality of segmental balloons are capable of being filled with air gas, liquid, low viscosity organic or non-organic polymers.

4. The resilient catheter of claim 1, further comprising a syringe, said syringe configured to be connected to said resilient tube of said catheter.

5. A method of treating a retinal detachment, in a minimally invasive way using an inflatable catheter, said method comprising:

directing a plurality of segmental balloons connected in series to a resilient tube of the catheter under the conjunctiva and above the sclera toward a retinal tear, each of the plurality of segmental balloons having balloon portions disposed on opposite sides of the resilient tube, the resilient tube extending through a central portion of each of the plurality of segmental balloons, a fiber optic disposed on an outside or inside of said resilient tube so as to enable viewing of the path of said resilient tube;

inflating the balloon portions disposed on the opposite sides of the resilient tube to produce a buckle inside the eye;

removing the fiber optic from the resilient tube;

clamping the resilient tube with a clamp or tying the resilient tube with a suture so as to prevent a pressure loss in the plurality of segmental balloons; and separating the plurality of segmental balloons from a remaining part of the catheter while the plurality of segmental balloons are left in place for a period of time so as to heal the retinal tear.

6. The method of claim 5, wherein the step of directing the plurality of segmental balloons under the conjunctiva and above the sclera comprises directing the plurality of segmental balloons between 180 degrees and 360 degrees around the eye towards the retinal tear.

7. The method of claim 5, wherein the step of directing the plurality of segmental balloons under the conjunctiva and above the sclera further comprises gradually inflating the balloon portions in a front section of the catheter intermittently to expand the conjunctiva as the catheter is pushed gradually forward towards the retinal tear.

8. The method of claim 5, wherein the step of inflating the balloon portions further comprises inflating one or more of the plurality of segmental balloons to a diameter between 3 mm and 7 mm.

9. The method of claim 5, wherein the step of separating the plurality of segmental balloons from a remaining part of the catheter further comprises cutting the resilient tube of the catheter to a predetermined distance of between 10 mm and 45 mm.

10. The method of claim 5, wherein the step of directing the plurality of segmental balloons under the conjunctiva and above the sclera further comprises guiding the catheter under the conjunctiva using light from the fiber optic.

11. The method of claim 5, further comprising the steps of:

before the step of directing the plurality of segmental balloons under the conjunctiva and above the sclera, loosening conjunctival tissue, and elevating the conjunctival tissue from the sclera; and creating a less than 3 mm incision in the eye so as to gain access to a subconjunctival space between the conjunctiva and the sclera.

12. A method of treating a retinal detachment, in a minimally invasive way using an inflatable catheter, said method comprising:

providing an inflatable catheter that includes a resilient tube and a plurality of segmental balloons connected in series to the resilient tube, each of the plurality of segmental balloons having balloon portions disposed on opposite sides of the resilient tube, the resilient tube extending through a central portion of each of the plurality of segmental balloons, a fiber optic disposed on an outside or inside of the resilient tube so as to enable viewing of the path of the resilient tube;

creating a small incision in an eye so as to gain access to a subconjunctival space between the conjunctiva and the sclera;

directing the plurality of segmental balloons in the subconjunctival space up to 360 degrees around the eye towards a retinal tear;

inflating the balloon portions disposed on the opposite sides of the resilient tube to produce a buckle inside the eye;

removing the fiber optic from the resilient tube;

clamping the resilient tube with a clamp or tying the resilient tube with a suture so as to prevent a pressure loss in the plurality of segmental balloons; and separating the plurality of segmental balloons from a remaining part of the catheter while the plurality of segmental balloons are left in place for a period of time so as to heal the retinal tear.

13. The method of claim 12, wherein the step of creating a small incision in the eye further comprises creating a less than 3 mm incision in the eye.

14. The method of claim 12, wherein the step of directing the plurality of segmental balloons in the subconjunctival space comprises directing the plurality of segmental balloons between 180 degrees and 360 degrees around the eye towards the retinal tear.

15. The method of claim 12, wherein the step of directing the plurality of segmental balloons in the subconjunctival space further comprises gradually inflating the balloon portions in a front section of the catheter intermittently to expand the subconjunctival space as the catheter is pushed gradually forward towards the retinal tear.

16. The method of claim 12, wherein the step of inflating the balloon portions further comprises inflating one or more of the plurality of segmental balloons to a diameter between 3 mm and 7 mm.

17. The method of claim 12, wherein the step of separating the plurality of segmental balloons from a remaining part of the catheter further comprises cutting the resilient tube of the catheter to a predetermined distance of between 10 mm and 45 mm.

18. The method of claim 12, wherein the step of directing the plurality of segmental balloons in the subconjunctival space further comprises guiding the catheter in the subconjunctival space using light from the fiber optic.

19. The method of claim 12, further comprising the step of:
   prior to the step of creating the small incision in the eye, determining a position of a retinal tear by indirect ophthalmoscopy, and marking the position of the retinal tear with a dye or diathermy.

* * * * *